United States Patent [19]
Boulay et al.

[11] Patent Number: 5,707,868
[45] Date of Patent: Jan. 13, 1998

[54] VARIABLE-VOLUME REACTOR-TYPE DEVICE AND PROCESS FOR CULTURING CELLULAR MATERIAL

[75] Inventors: Michel Boulay, Meulun; Alain Deloire, Reims; Marie-Claude Mauro, Orbais l'Abbaye; Alain Meybeck, Courbevoie; Guy Pierry; Jean-Noël Rabaud, both of Toulouse, all of France

[73] Assignee: I.V.M.H. Recherche, Nanterre, France

[21] Appl. No.: 331,639

[22] PCT Filed: May 6, 1993

[86] PCT No.: PCT/FR93/00437

§ 371 Date: Dec. 22, 1994

§ 102(e) Date: Dec. 22, 1994

[87] PCT Pub. No.: WO93/22420

PCT Pub. Date: Nov. 11, 1993

[30] Foreign Application Priority Data

May 6, 1992 [FR] France ................. 92 05579

[51] Int. Cl.$^6$ ................. C12M 1/36; C12N 5/02
[52] U.S. Cl. ................. 435/383; 435/394; 435/403; 435/410; 435/430.1; 435/243; 435/289.1; 435/286.5; 435/299.1
[58] Field of Search ................. 435/240.1, 240.2, 435/240.23, 240.24, 240.25, 243, 813, 289.1, 293.1, 299.1, 325, 383, 394, 395, 403, 410, 286.1, 286.5, 430, 430.1, 420, 41, 261

[56] References Cited

U.S. PATENT DOCUMENTS

| | | | |
|---|---|---|---|
| 3,027,305 | 3/1962 | Freeman | 435/299.1 |
| 4,286,061 | 8/1981 | Messing et al. | 435/176 |
| 5,143,847 | 9/1992 | Kawase et al. | 435/299.1 |
| 5,330,905 | 7/1994 | Kula et al. | 435/183 |

FOREIGN PATENT DOCUMENTS

| | | | |
|---|---|---|---|
| 269 086 | 6/1988 | European Pat. Off. | |
| 322 749 | 7/1989 | European Pat. Off. | |
| 0 431 464 | 6/1991 | European Pat. Off. | 435/299.1 |
| 473 011 | 3/1992 | European Pat. Off. | |
| 1 589 364 | 3/1970 | France | |
| 2 507 496 | 12/1982 | France | |
| 2 519 651 | 7/1983 | France | |
| 25 14 638 | 10/1976 | Germany | 435/299.1 |
| 33 27 541 | 2/1985 | Germany | |
| 63-36783 | 2/1988 | Japan | 435/299.1 |
| 544676 | 1/1977 | U.S.S.R. | 435/299.1 |

OTHER PUBLICATIONS

"Biogasanlagen: Nutzung des Mikrobiellen Lebensraums bie der Entsorgung" Stadlbauer et al, Chemiker-Zeitung, 108, Jan. 1984.

*Primary Examiner*—William H. Beisner
*Attorney, Agent, or Firm*—Pollock, Vande Sande & Priddy

[57] ABSTRACT

Reactor-type device for placing in contact solid particles with a liquid. The device comprises an enclosure, delimited by walls, to be filled with the liquid and containing the solid particles in contact with the liquid, and an arrangement for supplying and evacuating the liquid from the enclosure. At least one of the walls of the enclosure can be moved, thereby creating a variable volume. The invention also concerns reaction or culture processes using the device.

16 Claims, 3 Drawing Sheets

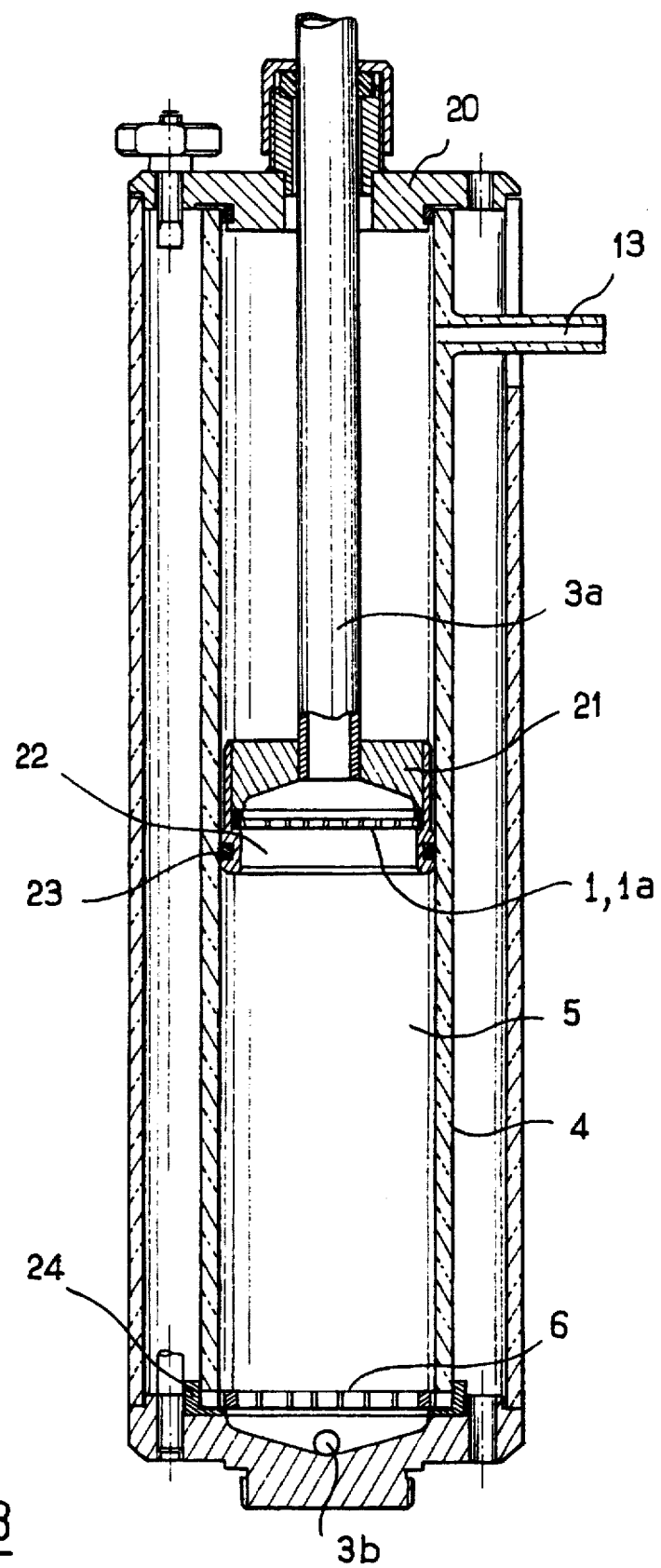
FIG_3

VARIABLE-VOLUME REACTOR-TYPE DEVICE AND PROCESS FOR CULTURING CELLULAR MATERIAL

FIELD OF THE INVENTION

The present invention relates to a device for culturing cellular biological material in the form of solid particles in the presence of a liquid culture medium. In this instance, "solid particles of cellular biological material" is understood to mean particles consisting, in all or in part, of cellular biological material, the other part, if appropriate, consisting of inert material such as a substrate or immobilization material. It can be, for example, cell clusters or parts of plant tissues such as pieces of roots or alternatively isolated cells coated onto inert substrates. As the said particles are generally fine, although not necessarily so, the device of the invention can, in fact, constitute a device for cell culturing in liquid medium, the said particles then comprising cells. This device contains an enclosure intended to be completely filled with the said liquid and to contain the said solid particles in contact with the liquid. It thus comprises means for supplying and discharging the liquid of the enclosure and means for retaining the said solid particles and for separating from the liquid in order to keep the solid particles within the enclosure in a specific region and optionally means for circulating and treating the liquid outside the enclosure. Another subject of the present invention is a process for carrying out the reaction of the particles with the liquid, especially a process for culturing cells in liquid medium using such a device.

BACKGROUND OF THE INVENTION

A reactor of this type has been described in International Patent Application WO 86 05202. However, the device described previously did not have a variable volume. Specifically, in certain cases, such as the culturing of plant somatic embryos, it appears that it can be advantageous, indeed necessary, to carry out culturing at a constant density by volume of cells in order to have correct development of the embryos or even to reduce this density by increasing the volume of the culturing enclosure, partly due to the release of certain compounds during maturation of the embryos, it being possible for these compounds to have a stimulating or inhibiting effect on the maturation.

Moreover, the reactor described in the abovementioned patent application contains, close to the culturing region, a helix (28) intended to create circulation of the liquid medium, such that it keeps the solid particles or cells in the condition of a fluidized bed. However, this arrangement includes the risk of injuring or detrimentally affecting the particles or cells, in particular if the latter escape from the fluidized bed, for example in the case of disturbance to or disfunctioning of the system.

SUMMARY OF THE INVENTION

An aim of the present invention is to provide a bioreactor which makes it possible to carry out culturing of cellular biological material at a constant cell density by volume during the development of the culture and, additionally, overcomes the disadvantages of the abovementioned reactor.

In order to do this, the present invention provides a device for culturing cellular biological material in the form of solid particles in which the said solid particles are brought into contact with a liquid culture medium, making it possible to keep the density by volume of the said cellular biological material substantially constant with respect to the volume of the said culture medium, containing:

a culture chamber consisting of an enclosure (5) delimited by walls, of which at least one of the said walls (1) can be movable so that the enclosure has a variable volume, means (3a and 3b) for supplying, discharging and circulating the liquid to and from the enclosure, and means (1a, 6) for retaining the said particles and for separating from the liquid in order to keep the particles within the enclosure, characterized in that it contains means, consisting of at least one of the said movable walls (1) of the enclosure, for varying the volume of the culture medium in the culture chamber, especially in order to increase the volume of the culture medium during the development of the culture and the increase in the volume of the cellular biological material.

In an embodiment of the device according to the invention, the enclosure defines, at least in part, a cylinder, the said movable wall of the enclosure consisting of a base of the cylinder.

In particular, the enclosure defines, at least in part, a cylinder which interacts in a leakproof way with a piston which can be moved within the cylinder so as to vary the volume of the enclosure as a function of its position, the base of the piston constituting a movable wall of the enclosure.

Appropriately, the enclosure consists of a cylindrical column, the means for supplying and discharging the liquid being situated at each end of the latter, one of these ends consisting of the said cylinder and the said piston, and the piston including a means for supplying or discharging the liquid of the enclosure at one of the ends of the column, another means for supplying or discharging the liquid being situated at the other end.

In a particularly useful embodiment, the abovementioned means for retaining the particles and for separating from the liquids can consist of two screens whose mesh does not allow the solid particles to pass, these means delimiting, with the other walls of the enclosure, a contact region between liquid and solid particles.

Advantageously, the meshing of the screens will be chosen especially as a function of one or a number of the following parameters, accessible to those skilled in the art: sizes and density of the particles with respect to the liquid medium, as well as the desired velocity of this medium, so that, in a specific embodiment of the invention, it is possible to keep the particles in the condition of a fluidized bed. For example, in the case where the particles are plant cell clusters, the meshing can be approximately 30 microns.

The size of the solid particles according to the invention can be chosen within a wide range. It is generally between 1 µm and 5 cm.

For particles greater than 20 µm, that is to say retained by meshes of 20 µm, the screens can, for example, consist of a cloth, especially made of stainless steel, set in a frame, or of a disc of sintered material such as sintered stainless steel.

For particles smaller than 20 µm, use is more likely to be made, as screens, of filtration membranes with pores smaller than the size of the particles.

The size of the meshes or pores of the screens or membranes respectively will be, according to the invention in general, from 0.5 µm to a few millimeters, for example 5 mm.

In a specific embodiment, the said movable wall, especially the base of the piston, incorporates a means for retaining the solid particles and for separating from the liquid, especially of the screen type as described above.

Appropriately, in the device according to the invention, the enclosure can consist of a cylindrical column containing a cylindrical wall and two end walls forming the bases of the said cylinder, the end walls containing screens which make possible the entry, the circulation and the departure of the liquid medium of the enclosure but which retain the particles within the enclosure, at least one of these two screens being movable.

In a specific embodiment of the device according to the invention, the enclosure contains an opening, which can be closed up, made in its wall, which makes it possible to introduce particles into the enclosure or alternatively to partially or completely introduce or withdraw the medium containing the solid particles. If appropriate, it will be preferable that the said opening communicates with the inside of the enclosure only when the enclosure reaches a certain volume, in particular when the volume of the enclosure is maximum. Thus, there is no risk of any disturbance being produced at the said opening during a culture or reaction process implemented with smaller enclosure volumes.

In general, the device according to the invention comprises means for circulating and treating the liquid outside the enclosure, especially containing a pipe, a pump, preferably with a variable flow rate and again preferably being of the type which makes it possible to reverse the direction of the stream of the liquid medium, and optionally a receptacle forming a reservoir for the liquid medium, and isolating clamps situated respectively at the inlet and at the outlet of the enclosure and of the said receptacle.

In particular, the said receptacle can contain various means for controlling, modifying and/or homogenizing the composition of the liquid medium, such as, for example, sensors for measuring the temperature, the pH or the concentration of the dissolved gases, and means for withdrawing from the medium or for adding various substances or compositions such as fresh medium or constituents of this medium, in the liquid, dissolved and/or gaseous form.

According to a specific embodiment, the device comprises an additional pipe, preferably equipped with an isolating clamp, which makes it possible to produce a loop for circulating the liquid medium, the said loop including the enclosure and the pump but isolating the abovementioned receptacle which forms the reservoir.

According to another specific embodiment, the device according to the invention additionally contains, especially at the said receptacle forming the reservoir, means which make it possible to draw off, alternately or continuously, at least part of the medium and to treat the latter, especially in order to extract substances, in particular those initially incorporated in the medium or those produced during the incubation of the medium with the said particles, and which make it possible, after the abovementioned treatment, optionally to recycle the withdrawn medium within the device, especially in the receptacle which forms the reservoir.

In particular, the abovementioned means advantageously comprise one or a number of extraction columns, arranged in series or in parallel, containing an appropriate chromatographic substrate.

It is understood that, when the particles consisting, for example, of cells or cell clusters are in suspension, it is possible to agitate them by means of the circulation of the liquid medium. So as to prevent, in this case, particles from gathering together in a region of the reactor and from no longer moving in the liquid, shapes will be avoided which can generate dead spaces.

Another subject of the present invention is a process for culturing cellular biological material in the form of solid particles in which the density by volume of the said material with respect to the volume of the culture medium in contact with the said particles in a culture chamber is kept substantially constant, characterized in that the volume of the culture medium included in the culture chamber is increased during the increase in the volume of the said material, by varying the volume of the culture chamber.

In an embodiment of the process, the said solid particles of the cellular biological material are brought into contact with the said liquid medium by means of a device according to the invention in which the enclosure is entirely filled with liquid and liquid culture medium is added within the abovementioned enclosure by increasing the volume of the said enclosure by moving the said movable wall, which makes it possible especially to control at will the density by volume of the said solid particles, by supplying culture medium during culturing.

According to an advantageous embodiment of the process of the invention, the said solid particles are kept suspended, at least intermittently, in the liquid medium, especially in the condition of a fluidized bed, by virtue of the circulation of this medium through the abovementioned enclosure.

Moreover, in an embodiment of the process of the invention, the liquid medium is circulated continuously or intermittently through the enclosure, optionally by regularly or irregularly reversing the direction of circulation, in order especially to obtain better agitation, as well as good distribution of the suspended particles in the enclosure and, if necessary, to clean the abovementioned retaining means, especially the screens.

As has been mentioned, when the device contains, outside the enclosure, circulation means comprising means for withdrawing the medium and means for adding fresh medium, it is possible to renew partially or entirely the liquid medium during reaction.

According to the invention, control and measurement of all the parameters of the reaction (temperature, $O_2$ content, $CO_2$ content, change in the contents of the compounds of the medium, and the like) is [sic] carried out outside the enclosure and during the reaction.

According to another characteristic of the process of the invention, it is possible, during reaction, continuously or intermittently to extract substances present in the liquid medium, whether they had been initially incorporated therein or whether they had been produced therein during the reaction, by virtue of the means described above, which make it possible to draw off, treat and/or recycle part of the medium.

According to a specific embodiment, the abovementioned particles consist entirely or partially of cellular biological material, it being possible for the other part, in the latter case, to consist of an inert material, advantageously a material generally used by those skilled in the art, especially as substrate or material for immobilization, in particular for inclusion, of the said cellular biological material.

The inert material, in particular that intended to be used to immobilize the said living material, can consist, for example, of a polymer matrix, such as a polyacrylamide, of an ionotropic gel, such as a carrageenan gel or a calcium alginate gel, of a high molecular weight protein, such as collagen in the microsponge form, or of glass, preferably in the form of porous beads.

The abovementioned cellular biological material can be composed of cells, such as eukaryote or prokaryote cells, especially microorganisms such as bacteria, molds, yeasts, euglenas or microalgae, plant cells, animal cells, differentiated or undifferentiated cell clusters, such as "TIL" (Tumor Infiltrating Lymphocytes), plant embryos or plant organs such as roots, tubers or organogenic nodules, or plantlets, such as micropopagules [sic] or protocorms, in particular orchid protocorms.

In particular, for the implementation of the process of the invention, flocculating-type microorganisms can be used. However, when the living material is composed of elements of very small size, such as isolated cells or microorganisms, especially yeasts or bacteria, it is generally preferred, for the implementation of the process of the invention, to immobilize the said elements, in an appropriate way known to those skilled in the art, for example by inclusion, by means of an inert material as defined above.

The culturing process according to the present invention can be applied advantageously to the production of somatic plant embryos, in particular of the vine or rose, by culturing embryogenic cell clusters, proembryogenic cell masses or proembryos or alternatively embryos which have already formed, such as embryos at the so-called globular, torpedo or cotyledonary stage.

An advantage of this type of process, especially applied to culturing a cellular biological material as defined above, in particular cells, cell clusters, plant embryos, plant organs or plantlets, is to be able to be freed from aerating the liquid medium directly in the culture chamber. In fact, aeration means such as oxygenation cartridges can be integrated with the means for treating the culture medium during circulation outside the culture chamber.

As more particularly concerns the "TIL", it is specified that, during their preparation, there is a stage in which they exist in the form of "pellet" particles, obtained after culturing for 7 days. Thus, at the "pellet" stage, the TIL can be introduced into the device of the invention for bulk production. The possibility which the device offers of being able to operate with a very low volume of medium, especially when the receptacle which forms a reservoir is taken off-line, is in this instance particularly advantageous because the culture medium is very expensive.

The device and the process according to the invention can be applied to the conversion of molecules by plant or animal cells or microorganisms when the said molecules are contained in the liquid medium.

It is possible, by the process according to the invention, to carry out the production of molecules, such as proteins, polyphenols such as flavonoids, saponins, terpenes, alkaloids, sterols, retinoids or vitamins.

BRIEF DESCRIPTION OF THE DRAWINGS

Other characteristics and advantages of the present invention will become apparent in the light of the detailed description which will follow, which is given solely by way of illustration and which consequently should not limit the scope of the invention in any way.

FIG. 3 represents, in cross section, an embodiment of the enclosure of the reactor.

DETAILED DESCRIPTION

Figure 1:
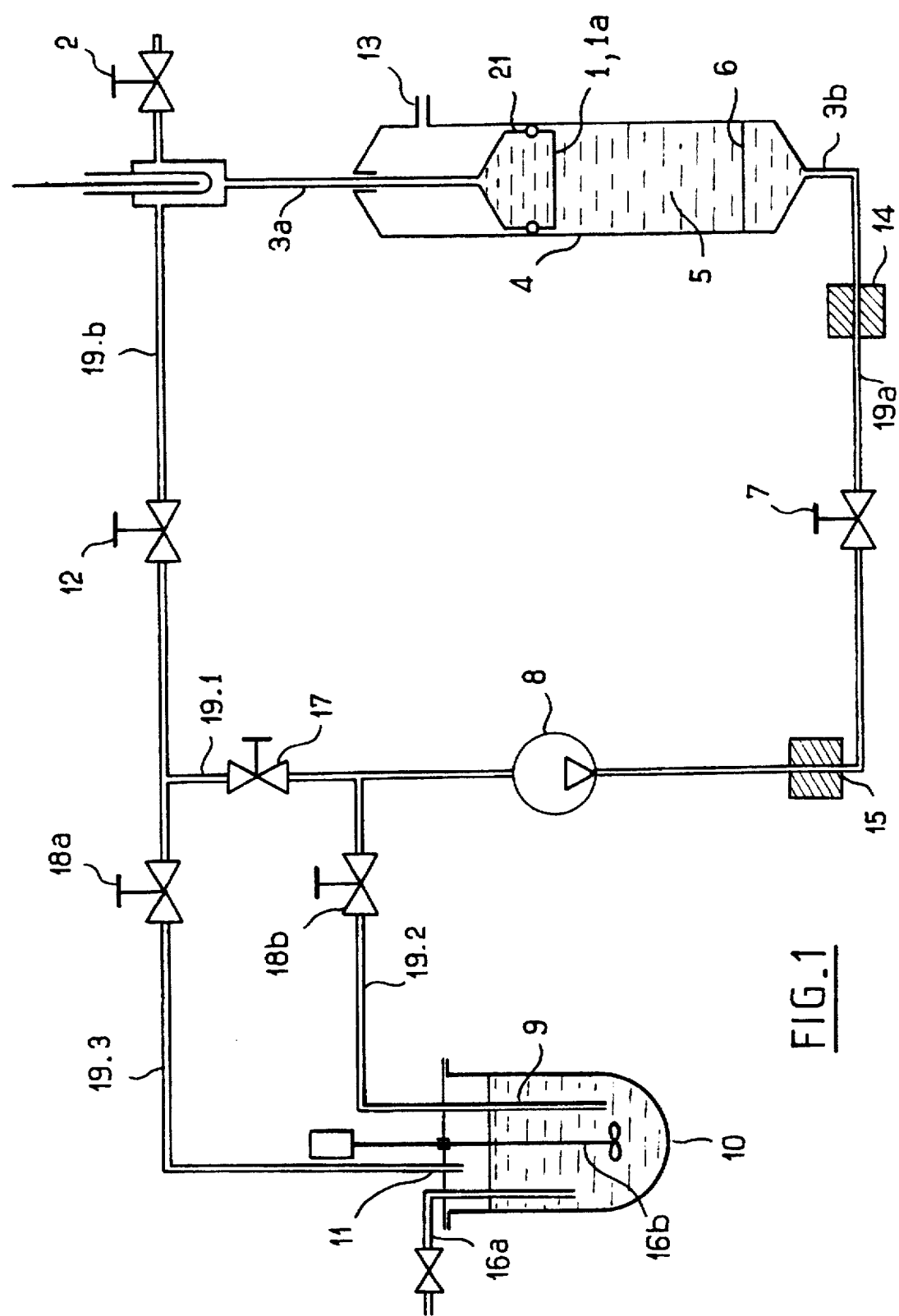
FIG. 1 represents a general diagram of a device according to the invention.
Figure 2:
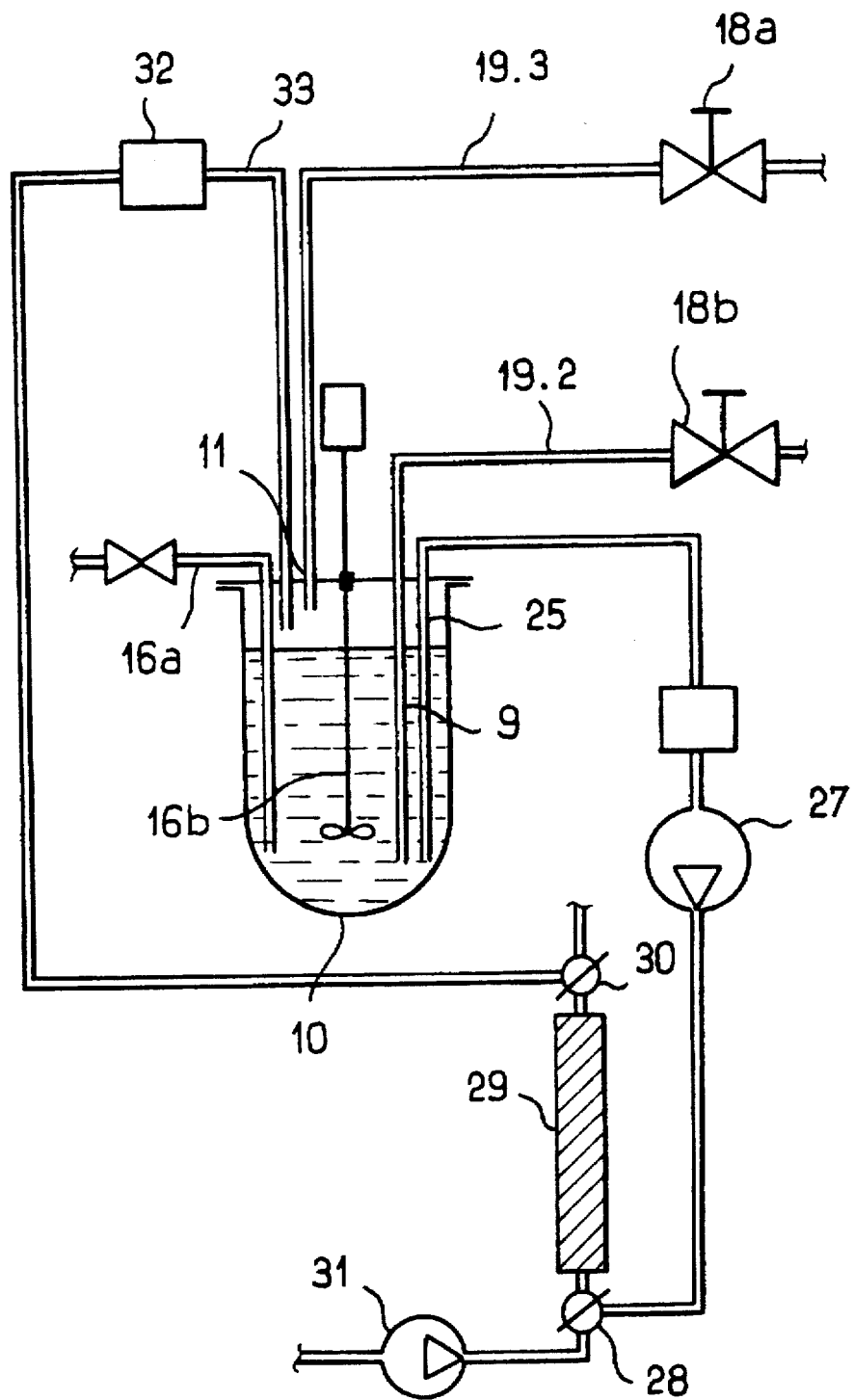
FIG. 2 represents an embodiment of the extraction means which make it possible to extract and separate substances from the liquid medium.

A device which is more particularly, but not exclusively, suited to cell culturing is described in FIGS. 1 to 3. The following are represented in the device of FIG. 1:

1=the movable wall of the enclosure

1a=screen, incorporated in the movable wall, for retaining the particles

2=a pipe and isolating clump for the pump for cleaning the screen

3a=the means for supplying and discharging the liquid of the enclosure into the piston for adjusting the working volume 3b=the means for supplying and discharging the liquid at the lower end of the enclosure 4=the cylindrical column 5=the variable-volume enclosure 6=a screen for retaining the particles 7=an isolating clamp 8=a variable—and/or reversible-flow circulation pump 9=a withdrawal pipe for the medium 10=a receptacle which forms a reservoir for the liquid medium 11=a return pipe for the medium 12=an isolating clamp 13=an opening, which can be closed up, especially for the introduction of cells into the enclosure 14=a sterilization filter 15=an oxygenation cartridge 16a=inlets for fresh culture medium or various gases by bubbling, such as $O_2$, $CO_2$, $N_2$ 16b =homogenizer of the medium 17, 18a, 18b=isolating clamps 19a, b, 19-1, 19-2, 19-3=pipes of the circuit outside the enclosure 21=the piston for adjusting the volume.

FIG. 1 [sic], the cylindrical column 4 constituting the variable-volume enclosure 5 is terminated at each of its ends by a conical shape. The movable wall 1 of the enclosure consists of the base of the piston 21. The piston interacts in a leakproof way with the interior of the cylindrical column 4 by an O-ring seal 23 (FIG. 3). The piston includes the means 3a for supplying or discharging the liquid at the upper end of the column 4. At the base of the column, the means 3b also make it possible to supply or discharge the liquid. The particles are retained in the enclosure by screens with a 30μ mesh, one (1a) enclosed in the base of the piston 21 and the other (6) at the base of the column.

In the example represented in FIGS. 1 and 3, when the piston is in the position where the enclosure has its maximum volume, the enclosure communicates with an opening 13 which makes it possible to introduce or withdraw liquid or to introduce particles into the enclosure.

Means for circulating and treating the liquid outside the enclosure, containing a pipe (19a, 19b, 19-1, 19-2, 19-3) and a variable-flow peristaltic pump 8, which makes it possible to vary the flow rate of the liquid medium and/or to reverse the direction of the stream, are represented in FIG. 1. As represented in FIG. 1, when the liquid circulates from the top downwards within the enclosure, it circulates outside via the pipes (3b, 19a, 19-1, 19-b, 3a), the clamps 18a and 18b are closed and the clamps 7, 17 and 12 are open. When the liquid circulates in the other direction, the liquid can circulate via the branch pipes 19-3 and 19-2, by passing via the receptacle-reservoir 10; in this case, it is necessary to open the clamps 18a and 18b and to close the clamp 17.

The conventional means for drawing off, extracting and separating substances from the liquid medium from the receptacle 10 are represented in FIG. 2:

25=a withdrawal pipe for extraction of compounds from the medium
26=a sterilization filter
27=a variable-flow circulation pump
28=a three-way valve
29=a chromatographic substrate column
30=a three-way valve
31=a variable-flow circulation pump
32=a sterilization filter
33=a return line of the medium after extraction of compounds.

In FIG. 2, the chromatographic substrate column can be imagined as being replaced by a number of different columns, in series or in parallel, in order to make possible the alternative extraction of different compounds.

The following are represented in FIG. 3, which shows an embodiment of an enclosure of the reactor suited in particular to culturing cells, cell clusters, embryos or roots:

20=the lid of the cylindrical column
21=the body of the piston
22=a cylindrical hood which is integral with the piston
23=an O-ring seal
24=a sheet gasket.

In FIG. 3, the lid 20 of the cylindrical column 4 is removable, which can make it possible, after having released the piston, to empty the solid particles such as roots, if appropriate.

In FIG. 3, the base of the cylinder 4 is arranged in abutment against the screen 6, which is itself in abutment against a sheet gasket 24 in a leakproof way.

A description is given below, by way of illustration, of a process for the regeneration of plant embryo production [sic], where the device and process according to the invention are involved in the three following stages of the process:

the propagation of embryogenic cells, of embryogenic cell clusters, of proembryogenic cell masses, of proembryos and/or of embryos at the globular stage, the development to embryos of embryogenic cell clusters, of proembryogenic cell masses or of proembryos and the maturation of the embryos thus formed, and the treatment phase of the embryos in order to induce their germination to plants.

It should be noted that, for reasons of simplification, the term "maturation" denotes, in the present description and the claims hereinbelow, both the development to embryos of cell clusters, of proembryogenic masses or of proembryos and the maturation proper of the embryos thus formed, these two processes being successive or more or less simultaneous depending on the culturing conditions and/or the plant species under consideration.

1) Filling the enclosure with culture medium

Maturation, as defined above, is begun in 80 ml of culture medium. The piston is raised to the position corresponding to this volume. The pipes 2 and 13 are closed.

The peristaltic pump 8 connected to the withdrawal pipe 9 and to the pipe 19a makes filling possible from the receptacle 10, via the pipe 3b at the bottom of the column. When the enclosure is filled, the medium leaves via the pipe 3a and then 19b via the top. The circuit is connected to the medium reservoir 10 by connecting the pipes 19b and 11 and the enclosure is filled and the whole is autoclaved for 20 minutes at 120° C. The reservoir contains approximately 1l of medium of Murashige and Skoog type which is well known to those skilled in the art, without growth hormone.

2) Introduction of cells in the form of clusters

After autoclaving, the device is placed under the flow of a hood in order to be handled sterilely. Pipes 2 and 13 are opened and the piston is raised as far as possible. 80 μl of cells are introduced in the form of clusters per ml of medium via the pipe 13 and rinsing is carried out with 1 ml of sterile medium. The piston is lowered as far as possible in order to remove air. The pipes 2 and 13 are then closed. The pump 8, which will make the liquid in the column 4 circulate, can then be operated, which will have the effect of suspending the fine clusters (200 μm to 500 μm) in the 80 ml of culture medium. Advantageously, the pump 8 is operated under conditions of variable flow, by alternating periods of significant flow and periods of low flow, or even zero flow, which has the effect of keeping the suspended clusters agitated. As a variant, in order to introduce the minimum amount of medium, 19a can be connected directly to 19b via the pipe 19-1 and circulation can be carried out in a closed circuit. Thus, the positive effect of certain growth factors generally has a beneficial result. Moreover, in this case, it is possible, and even advantageous, to operate the pump not only under variable conditions as described above but also alternatively in the reverse direction further in order to improve agitation of the clusters.

3) Culturing the somatic embryos

After culturing for four days, the volume of the culture is increased by raising the piston by a few centimeters. This is continued for 12 days, the volume being increased each day by approximately 30 ml in order to achieve a final volume of 450 to 500 ml (maximum volume of the chamber). It is also possible, two to three times during the culturing of the embryos, to completely renew the medium by emptying the column and the reservoir and by resupplying the receptacle 10 with fresh culture medium via the pipe 16a. This is carried out as for emptying and halting the circuit, as shown below.

4) Halting of the culturing of the somatic embryos

After having opened the pipe 2, the medium contained in the column is pumped towards the reservoir by the pump 8; the chamber 5 is emptied of medium and the embryos are deposited on the filter 6 (screen) at the bottom of the column 4. The column 4 (FIG. 3) is sterilely unscrewed and lifted up. The filter 6 and the embryos which have developed and which possess roots and cotyledons are recovered. It is now possible to separate them and to plant them out one by one on an appropriate substrate.

Comparative analysis:

1) First stage:
propagation of the cell clusters.

In the traditional culturing system, seeding is carried out at a density of 20 μl cells per ml, in 80 ml of medium, in a 250 ml Erlenmeyer flask. After culturing for 15 days, the density is 80 microliters per ml. At this density, splitting up into 4 Erlenmeyer flasks is necessary, if necrosis of the cells is not to take place. This operation is manual and the risk of microbial contamination is significant.

By virtue of the process of the device of the invention, using the movable piston, it is possible to bring the density to 20 μl of cell clusters per ml of medium by automatically adding culture medium without risk of exogenous contamination, which is an essential advantage for industrial implementation.

2) Second stage:
maturation and passing from the cell cluster stage to the embryo stage in the heart form.

In the traditional system, the starting density is from 1 to 2 μl of cells per ml and reaches 40 μl of cell clusters per ml after culturing for 15 days (in a 250 ml Erlenmeyer flask containing 80 ml of medium). It is necessary, during the 15 days of maturation, to remain at a density of 1 to 2 μl of cells per ml, if development of the cells to embryos is not to be blocked. A frequent manual supply of additional medium cannot be envisaged in an industrial application.

Moreover, the cells can release, into the medium, inhibitors of protein type and others, which it is problematic to remove from the Erlenmeyer flask.

The process and device of the invention make it possible to maintain the volumetric density of cell clusters as has been seen and, additionally, the coupling of an appropriate filtration system (25 to 33) to the circulation circuits outside the culture chamber 5 makes it possible to periodically or continuously remove the inhibitor-type molecules.

3) Third stage:

passing from the heart stage to the embryo stage having a root and two cotyledons.

In order to have correct development of the embryos, it is necessary, at this stage, to replace the culture medium by a different medium, this operation having to be carried out progressively. This operation is technically problematic in Erlenmeyer flasks.

The advantage of the process and device of the invention is there again decisive. Moreover, for maturation and treatment of the culture medium, the processes and devices of the invention make it possible to control and measure the various parameters: $O_2$, $CO_2$, $N_2$, temperature, agitation, PH [sic] and composition of the culture medium, without risk of damaging or injuring the embryos and the cell clusters.

We claim:

1. A process for culturing cellular biological material in the form of solid particles, said process comprising the steps of:

(a) providing a liquid culture medium in a culture chamber having a variable volume;
   (b) bringing said solid particles into contact with said liquid culture medium in said culture chamber;
   (c) increasing the volume of said culture medium contained in said culture chamber as appropriate during culturing and a corresponding increase in a volume of said biological material, by supplying additional culture medium and varying accordingly the volume of said culture chamber, thereby keeping the density by volume of said biological material substantially constant relative to the volume of said culture medium in contact with said particles in said culture chamber.

2. The process according to claim 1, wherein said culture chamber consists of:

(a) an enclosure delimited by walls, at least one of said walls being movable, so that the enclosure has a variable volume and is used for varying the volume of the culture medium in the culture chamber in order to increase the volume of the culture medium during culturing and corresponding increase in the volume of the biological material, said enclosure being entirely filled with liquid culture medium;
   (b) means for supplying, discharging and circulating the liquid to and from the enclosure, thereby forming inlet and outlet means of the enclosure; and
   (c) means for retaining said particles and for separating said particles from the liquid in order to keep the particles within the enclosures;
   (d) step (c) being performed by moving said at least one movable wall, which makes it possible to control at will the density by volume of said solid particles, by supplying culture medium during culturing.

3. The process according to claim 2, further comprising circulating and treating the liquid outside the enclosure, by means of:

(a) a pipe;
   (b) a variable flow rate pump of a type which makes it possible to reverse the direction of the stream of the liquid medium;
   (c) optionally a receptacle comprising a withdrawal pipe and a return pipe forming respectively an outlet and inlet of said receptacle, said receptacle forming a reservoir for the liquid medium; and
   (d) optionally, isolating clamps situated respectively at the inlet and at the outlet of the enclosure of said receptacle.

4. The process according to claim 2 or 3, wherein said solid particles are kept suspended, at least intermittently, in the liquid culture medium, by circulation of said medium through the enclosure.

5. The process according to claim 3, wherein the liquid culture medium is circulated continuously or intermittently through the enclosure, optionally by regularly or irregularly reversing the direction of circulation, in order to obtain better agitation as well as good distribution of the suspended particles in the enclosure and, if necessary, to clean the retaining means.

6. The process according to claim 2, wherein the liquid culture medium is at least partially renewed during reaction by means for withdrawing medium from and adding fresh medium to said culture chamber.

7. The process according to claim 2, wherein, during reaction, substances present in the liquid medium, whether initially incorporated in the liquid culture medium or produced therein during the reaction, are continuously or alternatively extracted and optionally recycled within the device by means adapted to draw off, treat and/or recycle part of said substances.

8. The process according to claim 2, wherein said solid particles consist at least partially of cellular biological material, a remainder consisting of an inert material selected from the group consisting of a substrate and material for immobilization, or inclusion of said cellular biological material.

9. The process according to claim 2, wherein said cellular biological material is composed of cells, selected from the group consisting of eukaryote cells, prokaryote cells, bacteria, molds, yeasts, euglenas, microalgae, plant cells, animal cells, differentiated or undifferentiated cell clusters, plant embryos, and plant organs.

10. The process according to claim 9, wherein said biological material is composed of cell clusters consisting of "TIL" (Tumor Infiltrating Lymphocytes).

11. The process according to claim 9, wherein said biological material is composed of plant organs selected from the group consisting of roots, tubers, organogenic nodules, plantlets, micropopagules, protocorms, orchid protocorms.

12. The process according to claim 2, for conversion of molecules by animal or plant cells or microorganisms when said molecules are contained in said liquid medium and when said cells or microorganisms are cultured.

13. The process according to claim 12, for production of molecules, selected for the group consisting of proteins, polyphenols, saponins, terpenes, alkaloids, sterols, retinoids and vitamins.

14. The process according to claim 2, for the production of somatic plant embryos, by culturing embryogenic cell clusters, preembryogenic cell masses or proembryos or embryos which have already formed.

15. The process according to claim 14, for the production of somatic plant embryos of a vine or rose.

16. The process according to claim 14 or 15, comprising culturing embryos at a globular, torpedo or cotyledonary stage.

* * * * *